United States Patent [19]

Hart

[11] Patent Number: 5,722,941
[45] Date of Patent: Mar. 3, 1998

[54] PNEUMATIC AMBULATORY TRACTION DEVICE

[76] Inventor: Brian K. Hart, 8225 N. 14th St., Kalamazoo, Mich. 49004

[21] Appl. No.: 603,978

[22] Filed: Feb. 20, 1996

[51] Int. Cl.$^6$ ........................................... A61F 5/00
[52] U.S. Cl. ................................. 602/32; 606/241
[58] Field of Search .................... 128/855, 878, 128/DIG. 20; 602/13, 32-35, 40, 240, 241

[56] References Cited

U.S. PATENT DOCUMENTS

| | | | |
|---|---|---|---|
| 2,665,685 | 1/1954 | Kaufman | 602/32 |
| 2,773,499 | 12/1956 | Nieden | 602/32 |
| 2,910,061 | 10/1959 | Rabjohn | 602/32 |
| 2,940,441 | 6/1960 | Demarest et al. | 602/32 |
| 3,086,518 | 4/1963 | Barlow et al. | 602/32 |
| 3,888,243 | 6/1975 | Powlan | 602/32 X |
| 3,937,216 | 2/1976 | Brown | 602/32 |
| 4,807,618 | 2/1989 | Auchinleck et al. | 128/878 |
| 5,181,904 | 1/1993 | Cook et al. | 602/32 |
| 5,470,316 | 11/1995 | Tovey et al. | 604/118 |

*Primary Examiner*—Richard J. Apley
*Assistant Examiner*—Denise Pothier
*Attorney, Agent, or Firm*—Edward J. Timmer

[57] ABSTRACT

A pneumatic ambulatory traction device comprises modular components that can be readily stowed at a facility or in a vehicle with minimum as-stowed space requirements and that can be readily and quickly assembled into a compact traction device usable at a facility, in a vehicle, at an accident site and the like to provide pneumatic traction force to a patient's body in a manner that can be controlled and varied as may be needed. The traction device comprises an elongated tubular housing connectable to a support, which may include an operating table or bed or a stretcher in a vehicle or at an accident site. A pneumatic cylinder is disposed in the housing and a piston is received in the cylinder and includes a piston rod movable in response to cylinder pressure to apply a traction force correlated to the cylinder pressure via a flexible cable connected to the piston rod and to a patient's body. A self-relieving pressure regulator is disposed on an exterior of the tubular housing and is communicated to the cylinder. The regulator includes a pressure control adjustment knob that is manually adjusted to provide a set cylinder pressure which will not be exceeded by virtue of the self-relieving pressure feature of the regulator. The traction force is controllable and varied by manual adjustment of the pressure control knob to provide the set cylinder pressure in dependence on the traction force to be applied to the patient's body. The traction device includes modular components for storage as a kit in a portable bag or case. For example, the traction device further includes a connector member receivable coaxially in the second end region of the tubular housing for joining the tubular housing to a hollow tubular extension housing to provide increased length to the tubular housing. Still further, the traction device may further include an elongated boom member releasably fastenable to the end region of the tubular housing or the extension post or housing, if employed, so as to extend laterally therefrom. The boom member includes a plurality of cable guide pulleys for directing the traction cable means in a particular manner depending on the particular region of the patient's body to be tractioned.

15 Claims, 4 Drawing Sheets

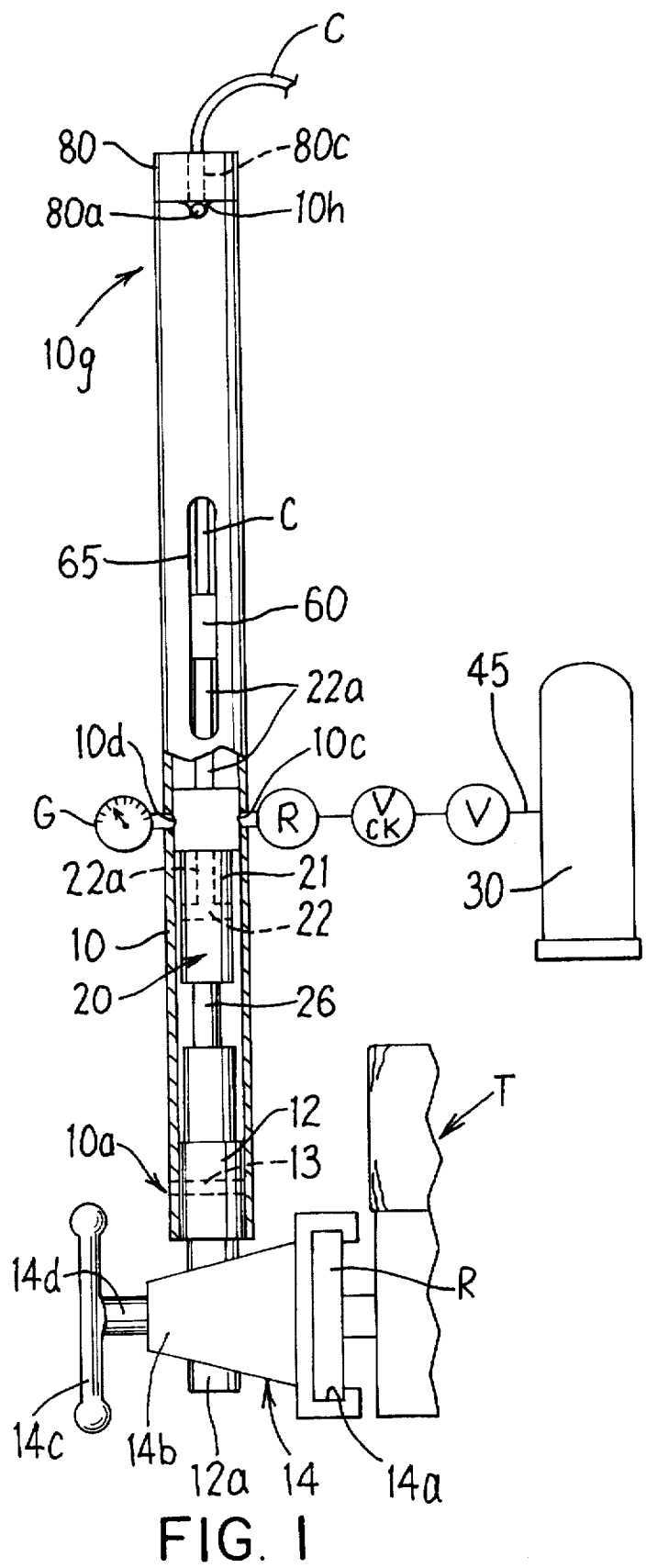
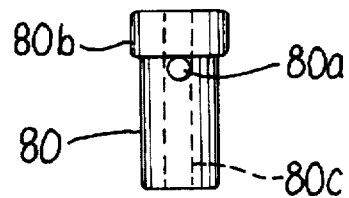
FIG. 2
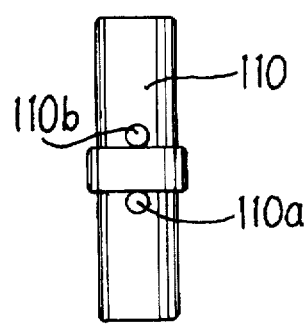
FIG. 3
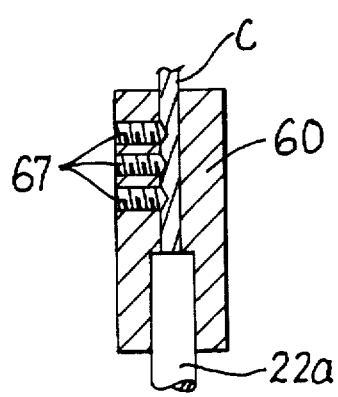
FIG. 4
FIG. 1

PNEUMATIC AMBULATORY TRACTION DEVICE

FIELD OF THE INVENTION

The present invention relates to a portable, modular, compact pneumatic ambulatory traction device that can be used to apply traction force to a patient's body in a wide variety of encountered situations such as in a hospital or emergency facility, in an EMS land, sea, or air vehicle, and at an accident site.

BACKGROUND OF THE INVENTION

Traditional traction devices for applying a traction force to a patient's body have involved the use of weights and tension lines (wires, rope, etc.) connected to a strap, belt, or other connector in turn connected a patient's body or appendage. One or more pulleys are sometimes used in conjunction with the tension lines depending upon the type of traction force to be applied and the appendage or other body region to be tractioned. The amount of weight is varied to vary the traction force on the patient's body or appendage.

During certain surgical procedures, a traction force is applied to the patient's body. For example, in shoulder arthroscopic surgery in which the patient is lying in a lateral or prone position, weights are positioned above the shoulder via a tension wire to apply tension on the shoulder. Unfortunately, the weights, tension wire and other support members of the traction device create obstacles in the operating arena for the surgeon and other personnel and must be avoided during the operation, complicating conduct of the surgical procedures.

Further, such traction devices are limited in use in that there is no way to quickly and accurately vary the amount of traction force as may be needed during a surgical procedure. Typically, the traction force is predetermined prior to the surgical procedure. A change in traction force from the predetermined level requires the addition or removal of weights. Oftentimes, additional weights may not be available or may not be available in the specific mass needed. This is disadvantgeous in that some surgical procedures will be performed best if the traction force can be readily varied from the predetermined level during the procedure.

Moreover, such weight/tension line traction devices are bulky and heavy and not readily transportable to or usable at accident sites. Further, such traction devices are not readily usable in the limited space available in emergency or rescue vehicles. Moreover, such traction devices can be time-consuming and difficult to set up in limited space environments such as may present in an emergency vehicle or at an accident scene. This is highly disadvantageous in that an accident victim may require the application of traction force immediately at an accident site in order to reduce the extent of injury.

SUMMARY OF THE INVENTION

The present invention provides a pneumatic ambulatory traction device that overcomes the aforementioned disadvantages. To this end, the traction device of the present invention comprises modular components that can be readily stowed at a facility or in a vehicle and that can be readily and quickly assembled into a compact traction device usable at a facility, in a vehicle, at an accident site and the like to provide traction to a patient's body in a manner that can be controlled and varied as may be needed.

An embodiment of the present invention provides a traction device comprising an elongated tubular housing having means for connecting an end region of the housing to a support, which may include for purposes of illustration only an operating table, hospital bed, transport cart, emergency stretcher in a vehicle or at an accident site. The connecting means preferably comprises a clamping stud or shaft fixed to an end region of the tubular housing and a clamp on the support for securely clamping the stud or shaft.

A pneumatic cylinder is disposed in the tubular housing with a piston received in the cylinder and including a piston rod movable in response to cylinder pressure to apply a traction force correlated to the cylinder pressure. The traction force is applied via flexible cable means connected between the piston rod and the patient's body. A self-relieving pressure regulator is disposed on an exterior of the tubular housing and is communicated to the cylinder. The regulator includes a pressure control adjustment member, such as a rotatable knob, that is manually adjusted to provide a set cylinder pressure which will not be exceeded by virtue of the self-relieving pressure feature of the regulator. The traction force is controllable and varied by manual adjustment of the pressure control member to provide a set cylinder pressure in dependence on the amount of traction force to be applied to the patient's body. A pressure gage is disposed on the tubular housing to display the cylinder pressure which, as mentioned, is correlated to traction force. A sight window or other means is provided to determine the extent of piston rod movement or stroke still available.

The tubular housing includes a second end region remote from the supported end region. The second end region may include an end slot that extends along a length of the housing. A cable guide member can be received in the second end region and have a detent that fits in the housing slot at that end region to prevent rotation of the cable guide relative to the housing.

The traction device of the present invention may include other moduluar components in addition to the cable guide. For example, in an embodiment of the present invention, the traction device further includes a connector member receivable coaxially in the second end region of the tubular housing with the connector member having a first detent received in the end slot of the housing to prevent relative rotation therebetween and a second detent remote from the first detent. A hollow tubular extension post or housing can be disposed on the connector member and have an end slot for receiving the second detent of the connector member to prevent rotation between the connector member and the extension post. The length of the tubular housing thus can be extended as needed by using one or more of such extension housings or posts.

Still further, the traction device may include an elongated boom member releasably fastenable to the end region of the tubular housing or to the extension post or housing, if employed, so as to extend laterally therefrom. The boom member includes one or more cable guide pulleys for directing the traction cable means in a particular manner depending on the particular region of the patient's body to be tractioned.

The modular components of the traction device can be conveniently stowed as a compact kit when not in use. In particular, a portable case, bag or other container can be provided in which the traction device housing, cable means, cable guide, connector members, extension posts or housings, and boom members can be stowed in a disassembled condition. The container can be conveniently located in EMR vehicles of all types for transport and use at accident sites, in the vehicle or as otherwise needed.

3

The aforementioned and other advantages and objects of the present invention will be better understood from the following detailed description of the invention taken with the following drawings.

DESCRIPTION OF THE DRAWINGS

FIG. 1 is an elevational view, partially in section, of an embodiment of the traction device pursuant to the invention and of an operating table to which the traction device can be clamped.

FIG. 2 is an elevational view of the cable guide member.

FIG. 3 is an elevational view of the housing connector member.

FIG. 4 is an elevational view of the cable connector member.

DESCRIPTION OF THE INVENTION

Figure 5:
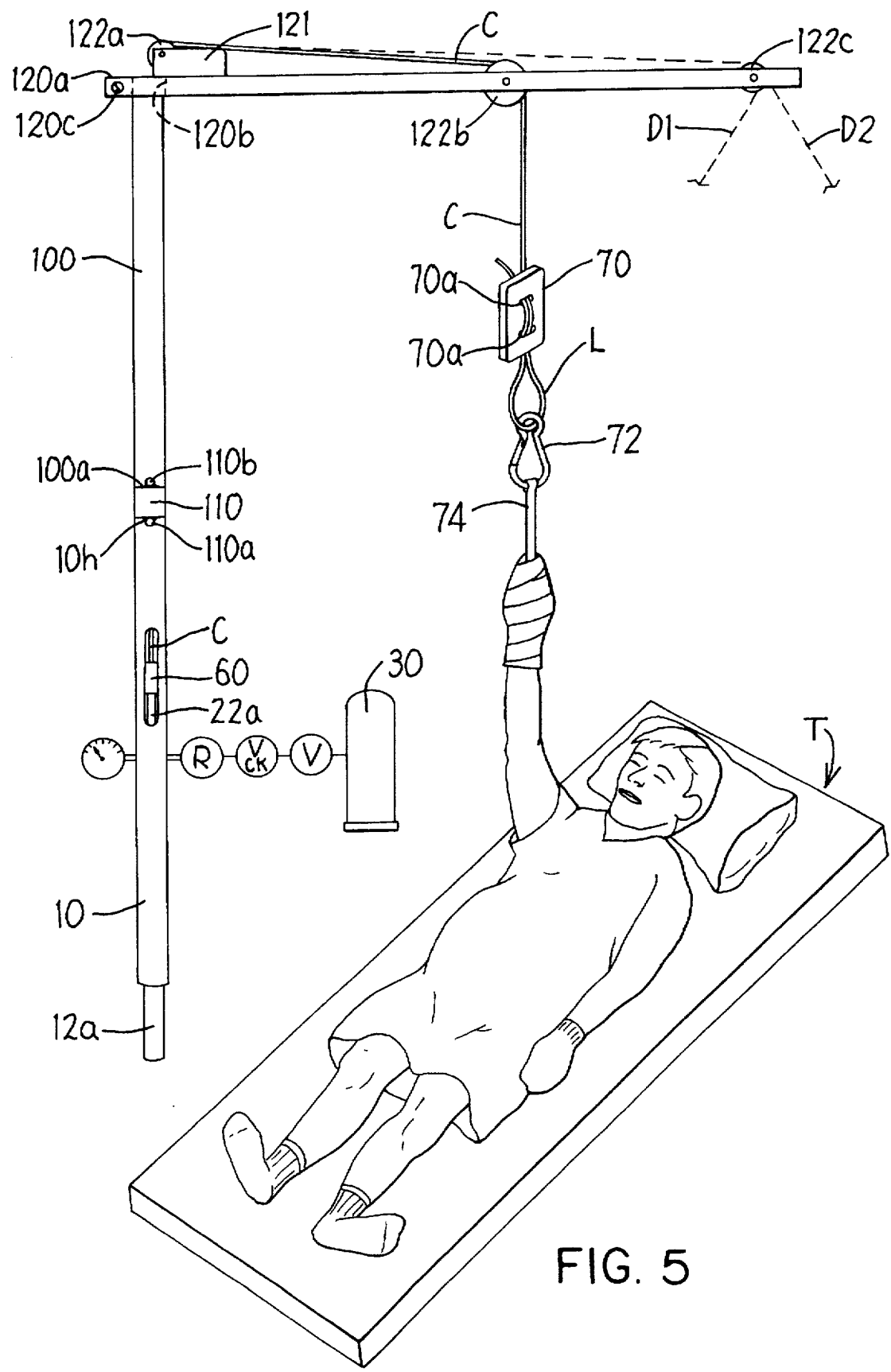
FIG. 5 is an elevational view of the modular components of the traction device assembled to provide traction force to an arm of a patient shown in perspective.

The present invention provides a pneumatic ambulatory traction device that comprises modular components that can be readily stowed at a facility or in a vehicle with minimum as-stowed space requirements and that can be readily and quickly assembled into a compact traction device usable at a hospital or other facility, in a vehicle, at an accident site and the like to provide traction to a patient's body in a manner that can be controlled and varied as may be needed.

Referring to FIGS. 1–6, an embodiment of the traction device of the present invention comprises an elongated, hollow outer tubular housing 10. An exemplary tubular housing 10 comprises Type 304 stainless steel and has a length of about 18 inches with an outer diameter of about 1 inch and inner diameter of 0.869 inches, although the invention is not limited to any particular dimensions. The tubular housing 10 includes a solid member 12 fixedly disposed in a first end region 10a. In particular, the solid insert member 12 is held fixed in the end housing region 10a by a cross-member 13 which can comprise a press-fit pin shown in FIG. 1 made of the same or different material as the housing 10. The solid insert member 12 defines a cylindrical end stud or shaft 12a disposed exterior of the housing 10. The stud or shaft 12a may have an exemplary length of 3 inches for clamping and diameter of 0.625 inch, although the invention is not limited in this regard.

As shown in FIG. 1, the stud or shaft 12a is adapted to be clamped by a clamp 14 or other connecting means to a support proximate the patient. The support is shown as an operating table T for purposes of illustration but can comprise any suitable support proximate the patient to be tractioned. For example, the support can comprise a hospital bed, transport cart, emergency stretcher in a vehicle or at an accident site, or support of other type.

The clamp 14 shown in FIG. 1 comprises a conventional operating table clamp having a slotted side 14a received on a rail R of the operating table, a clamping member 14b receiving the stud or shaft 12a of the traction device, and a clamp hand wheel 14c rotatable to cause a clamping shaft 14d to clamp the stud or shaft 12a. Such operating table clamps are well known and in widespread use. Other types of clamps capable of clamping the cylindrical stud or shaft 12a can be used in practicing the present invention. The stud or shaft 12a may have a shape other than the cylindrical shape shown to facilitate clamping.

A pneumatic cylinder 20 is disposed in the tubular housing 10 and includes a piston 22 received in the cylinder. The piston 22 includes a piston rod 22a that extends outside the cylinder in the housing and is movable with the piston in response to cylinder pressure. The cylinder pressure is used to move the piston 22 and piston rod 22a to apply a traction force that is correlated to the cylinder pressure.

The cylinder 20 is held in position in the housing 10 by a cylinder mounting member 26 disposed between the solid member 12 and the cylinder 20. In particular, the cylinder mounting member 26 comprises a shaft that is threaded into a threaded passage in the facing end of the solid insert member 12 and into a threaded passage in the facing end of the cylinder 20 in a manner to fix the cylinder in position in the housing 10. The threaded shaft can comprise a "⅛ inch" diameter galvanized or non-galvanized steel pipe (e.g. outer diameter of ¹³⁄₃₂ inch and inner diameter of approximately ¼ inch).

The piston 22 is disposed in a cylinder chamber 21 that is communicated to a source 30 of compressed medical gas, compressed air, or other compressed gas. For example, the source 30 can comprise compressed medical gas, such as compressed nitrogen or inert gas, that is commonly available in hospital operating and emergency rooms from conventional gas bottles or bulk sources. Alternatively, the source 30 can comprise compressed air that would be available at wall compressed air fittings in a surgery suite, emergency room, patient room, critical care room, and other rooms. However, any suitable compressed or pressurized gas can be used to pressurize the cylinder chamber 21 in the practice of the invention. The gas pressure typcially will be in the range of about 5 to 25 psig (gage pressure), for the pneumatic circuit components described below, although the invention is not so limited.

The cylinder chamber 21 is supplied with the source 30 via a flow control valve V, check valve V CK, and a self-relieving pressure regulator R as illustrated schematically in FIG. 1. Pressure in the cylinder chamber 21 is measured and displayed by a suitable pressure gage G having a pointer and dail to this end.

Figure 6:
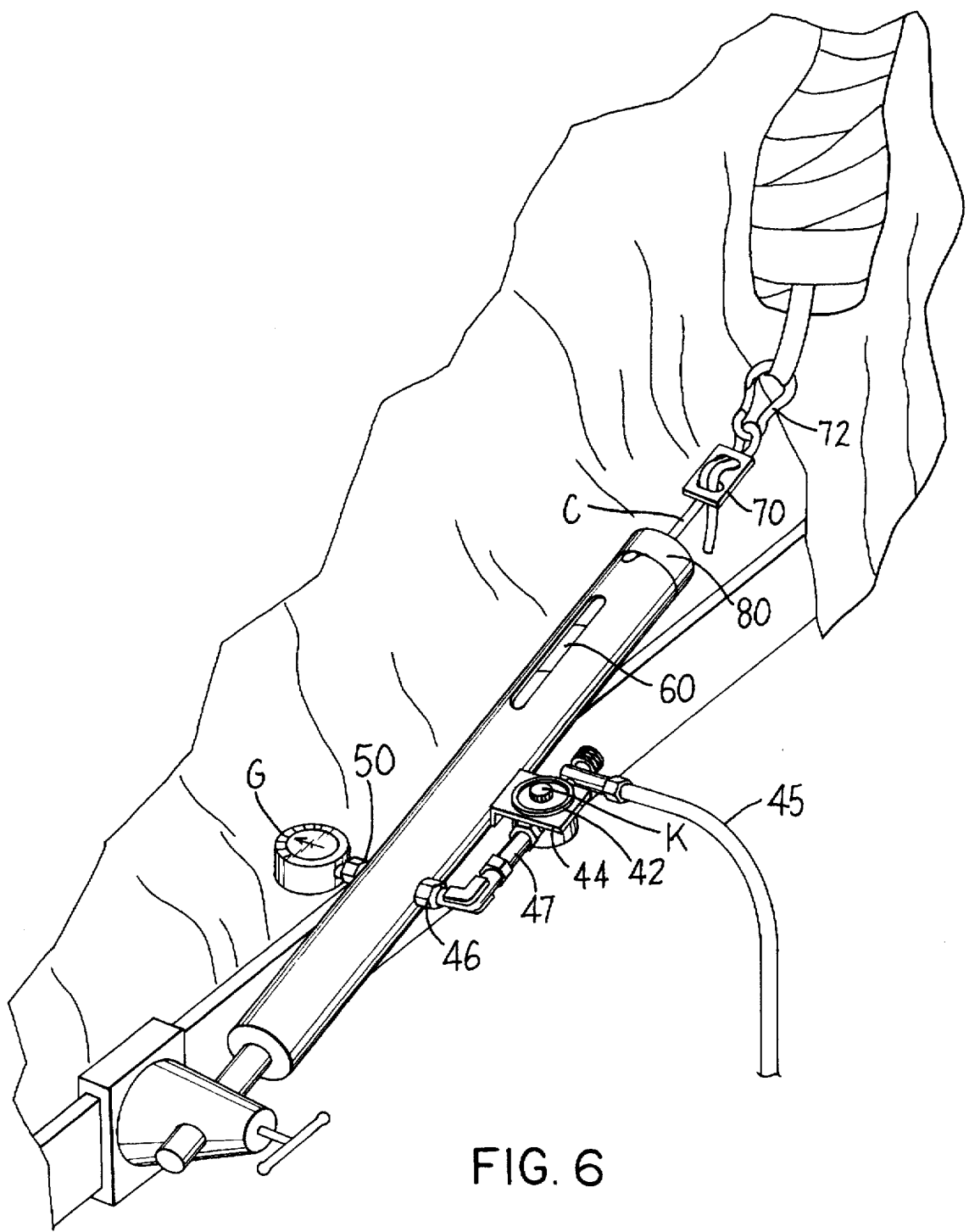
FIG. 6 is a perspective view of the tubular housing and pneumatic circuit components.

Referring to FIG. 6, the flow control valve V and check valve V CK are disposed on and communicated to the housing 42 of the self-relieving pressure regulator R. The housing 42 is fastened on the tubular housing 10 by a steel flange member 44 attached to the housing 10 by a weldment. A flexible pneuamtic hose 45 connects the source 30 to the flow control valve V and thus to the check valve V CK and self-relieving pressure regulator R. The regulator R is connected to a short length of flexible pneumatic hose 47 that in turn is connected to a rigid pipe fitting 46. The fitting 46 is threaded into a threaded port of the cylinder 20 in a manner to communicate to the cylinder chamber 21. The pipe fitting 46 extends through a suitable hole 10c in the tubular housing 10 to this end.

The pressure gage G is connected to another threaded port of the cylinder 20 in a manner to communicate to the cylinder chamber 21. The gage fitting 50 extends through a suitable hole 10d in the tubular housing 10 to this end.

The flow control valve V functions to limit the speed that air enters the chamber 21. The flow control valve V can comprise a conventional flow control valve commercially available as model number FCP2 from Bimba Manufacturing Co., Monee, Ill. The check valve V CK functions to maintain pressure on the cylinder while changing a pressure source and can comprise a conventional check valve commercially available as model number C200B from Parker Hannifin Corporation, Cleveland, Ohio.

The self-relieving pressure regulator R includes a pressure control adjustment member, such as a rotatable knob K in FIG. 6, that is manually adjusted to provide a set cylinder pressure (i.e. pressure in cylinder chamber 21) which will not be exceeded by virtue of the self-relieving pressure feature of the regulator R. To this end, the regulator R can comprise a conventional self-relieving pressure regulator commercially available from Watt's Fluidair Inc., Kittery, Me. 03904. Such a self-relieving pressure regulator will have pressure control range of 0 to 125 psi. The knob K can be used to set any given maximum cylinder pressure within this range, which maximum cylinder pressure will not be exceeded by virtue of the self-relieving pressure feature of the regulator R. That is, any cylinder pressure exceeding this set maximum value will be relieved by the regulator R typically by venting to ambient atmosphere to return cylinder pressure to the set value.

The traction force applied to the patient is controllable and varied by manual adjustment of the pressure control member (knob K) to provide the set cylinder pressure in dependence on the traction force to be applied to the patient's body. The traction force applied to the patient is correlated to the cylinder pressure; e.g 1 psi of cylinder pressure approximately equals one pound of traction force. Thus, operation of the traction device to provide a particular predetermined, controlled traction force is simple in that the operator simply turns the knob K on the regulator R to set a desired pressure at which cylinder pressure will remain. The operator can adjust the traction force as needed simply and conveniently by rotating the knob K to increase or decrease the self-relieving pressure of the regulator R. The dial gage G indicates to the operator the amount of cylinder pressure and is the guideline for the amount of traction that is being applied based on the aforementioned correlation between cylinder pressure and traction force.

The traction force is applied to the patient by a flexible cable C connected to the piston rod 22a via a cable connector 60 shown in FIG. 4. The cable typically comprises vinyl coated stainless steel cable but may include other suitable flexible connector such wire, rope, and the like. The end of the piston rod 22a is threadedly received and held in the connector 60 and the end of the cable C is held by three lock screws 67. In this way, movement of the piston rod 22a in response to cylinder pressure is transmitted to the cable C.

The housing 10 includes a sight window 65 that is cut out of the housing along the length thereof in a manner to expose the piston rod 22a and cable connector 60 to view from exterior of the housing 10 so that the extent of piston rod movement or stroke can be visually determined. In this way, the operator of the traction device can determine the relative position of the piston rod 22a and the amount of additional movement available to use. Other means that could be used to determine the location of the piston rod 22a could include a proximity sensor and other rod sensing or viewing devices.

The other opposite end of the cable C is releasably connected to a cable slip lock member 70 of the invention shown in FIG. 5. In particular, the cable C is looped through two spaced apart holes 70a in the slip lock member 70 in a manner that forms a loop L and secures the cable end to the slip lock member 70 to prevent cable loosening or movement. A suitable connector clip or latch 72 can be connected to the cable loop L. The clip or latch 72 typically is connected to a strap 74 secured by a doctor or other personnel to the patient's appendage; e.g. the patient's arm as shown in FIG. 5, to which traction is to be applied.

In use of the traction device of the present invention described hereabove, the cable C can be connected directly between the piston rod 22a and the patient's appendage as shown, for example, in FIG. 6.

To this end, the tubular housing 10 includes a second end region 10g remote from the supported end region 10a (where the stud or shaft 12a is clamped). The second region includes an end slot 10h that extends along a length of the housing. A cable guide member 80 is received in the second end region 10g when the cable is connected directly between the piston rod 22a and the patient's appendage as shown in FIG. 6.

The cable guide member 80 has a raised, cylindrical detent 80a that fits in the housing slot 10h at the end region 10g to prevent rotation of the cable guide 80 relative to the housing 10 as shown in FIG. 1. The cable guide 80 includes the raised cylindrical detent 80a adjacent a diametrically enlarged collar 80b that rests on the end region 10g of the housing 10 and a central passage 80c through which the cable C extends from the piston rod, see FIGS. 1 and 2. Cable guide member 80 may comprise 6061T651 aluminum.

In other uses of the traction device of the present invention, the cable C can be connected between the piston rod 22a and the patient's appendage using additional modular components as shown, for example, in FIG. 5. In the embodiment of the invention shown in FIG. 5, the traction device includes a hollow, cylindrical extension housing or post 100 joined to the primary tubular housing 10 by a connector member 110. The extension post 100 may be made of the same material as the housing 10 and have similar dimensions. Connector member 110 can be made of 6061T651 aluminum and includes a central passage for passage of the cable C.

The invention envisions a kit of components wherein several extension posts 100 are provided having different lengths such as 12 inches and 18 inches for use with the tubular housing 10 as needed in a given situation.

The connector member 110 is received coaxially in the second end region 10g of the tubular housing 10 with a first raised, cylindrical detent 110a received in the housing end slot 10h to prevent relative rotation therebetween. The connector member 110 includes a second raised, cylindrical detent 110b remote from the first detent 110a. The hollow tubular extension post or housing 100 can be disposed on the connector member 110 and includes a first end slot 100a for receiving the second detent 110b of the connector member to prevent rotation between the connector member and the extension post. A second end slot (not shown but like slot 100a) is provided at the opposite end of the extension post 100 in the event a second extension post (not shown but similar to post 100) is mounted on the first extension post 100 by using a second connector member 110 to further increase the length of the traction housing. The second post can have the same or different length as the first extension post 100. For example, two 12 inch long extension posts can be mounted atop one another or a 12 inch post and 18 inch post can be mounted atop one another by using a connector member 110 at the joint. The length of the traction housing thus can be extended as needed to apply a traction force.

The kit of components envisioned by the invention also can include one or more elongated boom members 120 releasably fastenable to the end region 10g of the tubular housing 10 or to the end of the extension post 100, if employed, as shown for example in FIG. 5. The boom member 120 shown in FIG. 5 extends laterally from and perpendicular to the post 100 and includes a guide block 121 and first, second, and third cable guide pulleys 122a, 122b, 122c for directing the traction cable C in a particular manner depending on the particular region of the patient's body to be tractioned. In FIG. 5, cable C is shown in solid lines passing over pulleys 122a and 122b to the patient's arm for applying traction to the shoulder during arthroscopic shoulder surgery. In FIG. 5, cable C is shown in phantom lines passing over pulleys 122a and 122c as an alternative cable route for applying traction force in a different manner. The cable can be directed within a range of direction between D1 and D2 at pulley 122c. The same range of direction is available at pulley 122b if that cable routing is used. The pulleys can comprise food-grade DELRIN (trademark of DuPont) plastic material.

The boom member 120 includes a slotted end 120a communicating to a circular cut-out region 120b that receives the end region of the housing 10 or extension post 100, as the case may be. The end region of the housing 10 or post 100 is received in the cut-out region 120b and is clamped thereon by tightening a bolt 120c extending through a passage through the slotted end 120a. The kit of components can include boom members 120 of different length; e.g. a 24 inch boom member having pulleys 122a, 122b, 122c as shown in FIG. 5 and a 36 inch boom member (not shown) having pulleys 122a and 122c but not pulley 122b.

Figure 7:
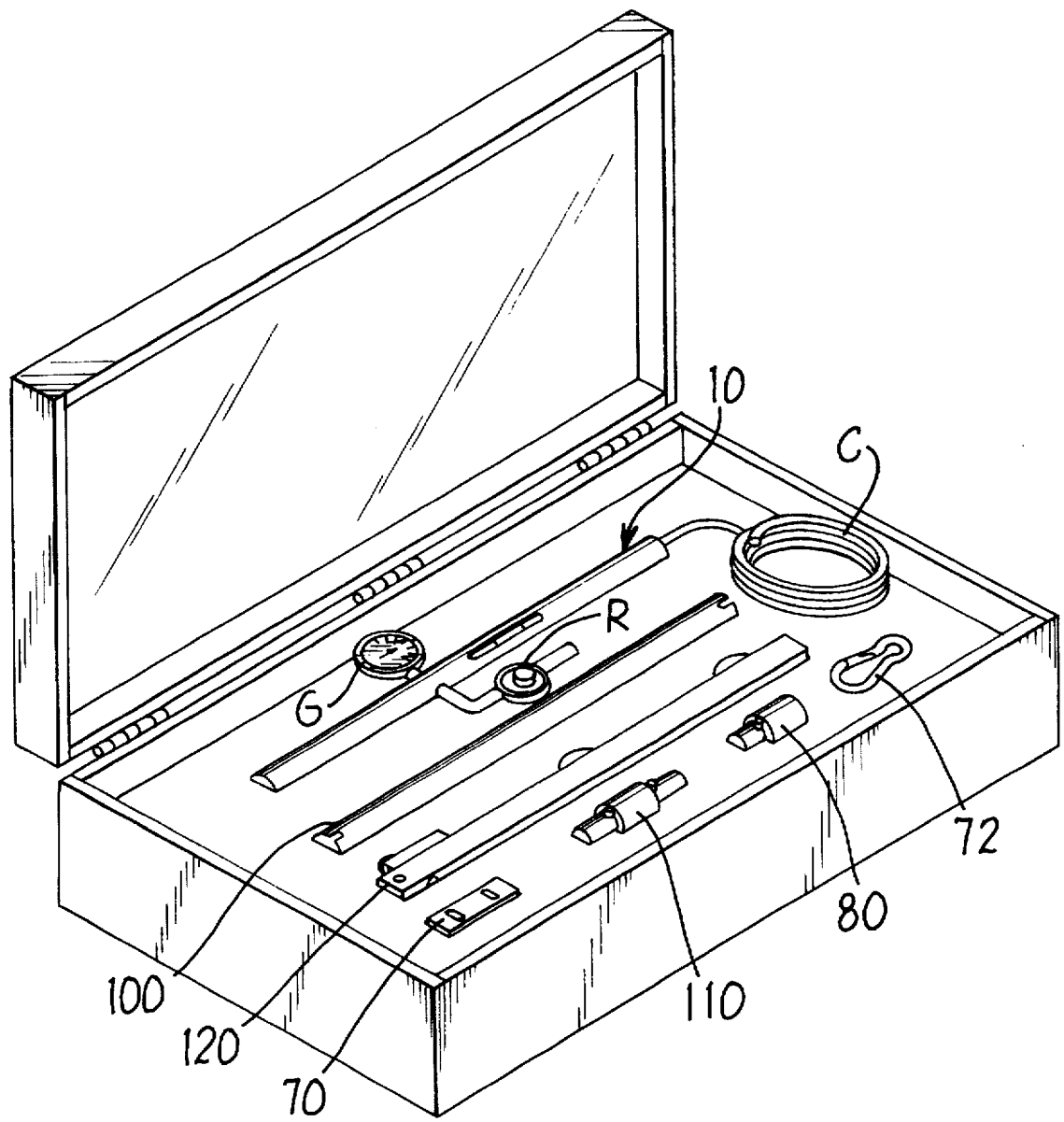
FIG. 7 is a perspective view of the components of the traction device as a kit in disassembled condition in a rigid case.

The modular components of the traction device can be conveniently stowed as a compact kit when not in use. In particular, a portable case, bag or other container can be provided in which the traction device tubular housing 10, cable C, cable slip lock 70, cable guide member 80, extension housings or posts 100, connector members 110, and boom members 120 can be stowed in a disassembled condition. The case, bag or container can be conveniently located in EMR vehicles of all types for transport and use at accident sites, in the vehicle or as otherwise needed. FIG. 7 illustrates a rigid case in which these modular kit components are carried in the disassembled condition. A flexible cloth or plastic bag or other container also can be used in transporting the kit.

The traction device of the present invention can be used to apply traction to a patient's joints or vertebrae wherein the traction force is controlled by adjustment of the pressure control knob described hereabove of the self-relieving pressure regulator R. Uses of the traction device include, but are not limited to, shoulder and ankle traction during arthroscopy, above and below the knee traction, femoral traction, and cervical traction. The traction device can be used in surgery, radiology, emergency room, patient room, chiropractic treatment, physical therapy, and EMS air, land, and sea vehicles using an operating table, hospital bed, transport cart, emergency stretcher, and the like as a support for the traction device. Moreover, the traction device can apply traction in any direction including against gravity.

While the invention has been described in terms of specific embodiments thereof, it is not intended to be limited thereto and changes and modifications can be made therein without departing from the spirit and scope of the invention as set forth in the following claims.

I claim:
1. A traction device comprising an elongated tubular housing including means for connecting an end region of said housing to a support, a pneumatic cylinder received in said housing, a piston received in said cylinder and having a piston rod movable relative to said housing to apply a traction force correlated to pneumatic pressure in said cylinder via flexible cable means connected to said piston and connected to a patient's body, a self-relieving pressure regulator disposed on an exterior of said housing and communicated to said cylinder, said regulator having a pressure control adjustment member that is manually adjusted to provide a set cylinder pressure which will not be exceeded during application of traction force by said self-relieving regulator venting excess pressure to ambient atmosphere, said traction force being controllable by manual adjustment of said pressure control adjustment member to provide said set cylinder pressure for a traction force to be applied to the patient's body, a pressure gage disposed on said housing to display said cylinder pressure, and means disposed on said housing for determining the extent of piston rod movement.

2. The device of claim 1 wherein said housing comprises a cylindrical tube.

3. The device of claim 1 wherein said means for connecting an end region of said housing to said support comprises a clamping stud fixed to said end region and clamping means for clamping said stud to said support.

4. The device of claim 1 wherein said pressure control member comprises a manually rotable knob on said regulator.

5. The device of claim 1 wherein said means for determining the extent of piston rod movement comprises a sight window in said tubular housing.

6. The device of claim 1 wherein said housing includes a second end region remote from the supported region, said second region including a slot that extends along a length of said housing and terminates at said second end in an open end, a cable guide member positioned in said open end.

7. The device of claim 6 further including a cable guide member received in said second end region and having a detent that fits in said slot to prevent rotation of said cable guide relative to said housing.

8. The device of claim 6 further including a connector member received coaxially in said second end region of said housing, said connector member having a first detent received in said slot of said housing to prevent relative rotation therebetween and a second detent remote from said first detent, and a hollow tubular extension housing disposed on said connector member and having an end slot receiving said second detent to prevent rotation between said connector member and said extension housing.

9. The device of claim 1 further including an elongated boom member releasably fastened to a second end region of said housing and extending laterally therefrom, said boom member having one or more cable guide pulleys.

10. The device of claim 1 further including a slip lock member having first and second holes through which said cable means is passed to form a cable loop.

11. A traction kit including a traction device comprising an elongated tubular housing including means for connecting an end region of said housing to a support, said housing including a second end region remote from the supported region and including a slot that extends along a length of said housing, a connector member for being received coaxially in said second end region of said housing, said connector member having a first detent for receiving in said slot to prevent relative rotation between said housing and said connector member and a second detent remote from said first detent, a tubular extension housing for positioning on said connector member and having an end slot for receiving said second detent to prevent relative rotation between said connector member and said extension housing, a pneumatic cylinder received in said housing, a piston received in said cylinder and having a piston rod movable relative to said housing to apply a traction force correlated to pneumatic pressure in said cylinder via flexible cable means connected to said piston and connected to a patient's body, a self-relieving pressure regulator disposed on an exterior of said housing and communicated to said cylinder, said regulator having a pressure control adjustment member that is manually adjusted to provide a set cylinder pressure which will not be exceeded, said traction force being controllable by manual adjustment of said pressure control adjustment member to provide said set cylinder pressure for a traction force to be applied to the patient's body, a pressure gage disposed on said housing to display said cylinder pressure, and means for determining the extent of piston rod movement, and further including a portable container in which said tubular housing, said cable means, said connector member, and said extension housing can be stowed in a disassembled condition.

12. The traction kit of claim 11 wherein said container comprises a bag or rigid case.

13. A traction device comprising an elongated tubular housing including means for connecting an end region of said housing to a support, said housing including a second end region remote from the supported region and including a slot that extends along a length of said housing, a cable guide member received in said second end region and having a detent that fits in said slot to prevent rotation of said cable guide member relative to said housing, a pneumatic cylinder received in said housing, a piston received in said cylinder and having a piston rod movable relative to said housing to apply a traction force correlated to pneumatic pressure in said cylinder via flexible cable means connected to said piston and connected to a patient's body, a self-relieving pressure regulator disposed on an exterior of said housing and communicated to said cylinder, said regulator having a pressure control adjustment member that is manually adjusted to provide a set cylinder pressure which will not be exceeded, said traction force being controllable by manual adjustment of said pressure control adjustment member to provide said set cylinder pressure for a traction force to be applied to the patient's body, a pressure gage disposed on said housing to display said cylinder pressure, and means for determining the extent of piston rod movement.

14. A traction device comprising an elongated tubular housing including means for connecting an end region of said housing to a support, said housing including a second end region remote from the supported region and including a slot that extends along a length of said housing, a connector member received coaxially in said second end region of said housing, said connector member having a first detent received in said slot to prevent relative rotation between said housing and said connector member and a second detent remote from said first detent, a tubular extension housing disposed on said connector member and having an end slot receiving said second detent to prevent relative rotation between said connector member and said extension housing, a pneumatic cylinder received in said housing, a piston received in said cylinder and having a piston rod movable relative to said housing to apply a traction force correlated to pneumatic pressure in said cylinder via flexible cable means connected to said piston and connected to a patient's body, a self-relieving pressure regulator disposed on an exterior of said housing and communicated to said cylinder, said regulator having a pressure control adjustment member that is manually adjusted to provide a set cylinder pressure which will not be exceeded, said traction force being controllable by manual adjustment of said pressure control adjustment member to provide said set cylinder pressure for a traction force to be applied to the patient's body, a pressure gage disposed on said housing to display said cylinder pressure, and means for determining the extent of piston rod movement.

15. The device of claim 14 further including an elongated boom member releasably fastened to an extension housing and extending laterally therefrom, said boom member having one or more cable guide pulleys.

* * * * *

UNITED STATES PATENT AND TRADEMARK OFFICE
CERTIFICATE OF CORRECTION

PATENT NO. : 5,722,941
DATED : March 3, 1998
INVENTOR(S) : Brian K. HART

It is certified that error appears in the above-indentified patent and that said Letters Patent is hereby corrected as shown below:

Column 8, line 36; delete ",a cable guide member positioned in said open end".

Signed and Sealed this

Eleventh Day of August 1998

Attest:

BRUCE LEHMAN

Attesting Officer

Commissioner of Patents and Trademarks